United States Patent
Kettenberger et al.

(10) Patent No.: US 11,577,005 B2
(45) Date of Patent: Feb. 14, 2023

(54) COMPOSITION FOR BONE REGENERATION

(71) Applicant: École Polytechnique Fédérale de Lausanne (EPFL), Lausanne (CH)

(72) Inventors: Ulrike Kettenberger, Lausanne (CH); Dominique Pioletti, Buchillon (CH)

(73) Assignee: ÉCOLE POLYTECHNIQUE FÉDÉRALE DE LAUSANNE (EPFL), Lausanne (CH)

( * ) Notice: Subject to any disclaimer, the term of this patent is extended or adjusted under 35 U.S.C. 154(b) by 415 days.

(21) Appl. No.: 15/757,207

(22) PCT Filed: Sep. 14, 2015

(86) PCT No.: PCT/CH2015/000133
§ 371 (c)(1),
(2) Date: Mar. 2, 2018

(87) PCT Pub. No.: WO2017/045084
PCT Pub. Date: Mar. 23, 2017

(65) Prior Publication Data
US 2018/0264175 A1    Sep. 20, 2018

(51) Int. Cl.
| | |
|---|---|
| A61L 27/52 | (2006.01) |
| A61C 17/02 | (2006.01) |
| A61L 27/46 | (2006.01) |
| A61L 27/54 | (2006.01) |
| A61L 27/58 | (2006.01) |
| A61C 8/00 | (2006.01) |
| A61C 19/06 | (2006.01) |
| A61M 5/32 | (2006.01) |
| A61B 17/16 | (2006.01) |
| A61C 17/022 | (2006.01) |
| A61C 17/20 | (2006.01) |

(52) U.S. Cl.
CPC ............ *A61L 27/52* (2013.01); *A61C 8/0092* (2013.01); *A61C 19/06* (2013.01); *A61L 27/46* (2013.01); *A61L 27/54* (2013.01); *A61L 27/58* (2013.01); *A61M 5/32* (2013.01); *A61B 17/1604* (2013.01); *A61B 17/1635* (2013.01); *A61C 17/02* (2013.01); *A61C 17/022* (2013.01); *A61C 17/20* (2013.01); *A61L 2400/06* (2013.01); *A61L 2430/02* (2013.01); *A61M 2210/02* (2013.01)

(58) Field of Classification Search
CPC combination set(s) only.
See application file for complete search history.

(56) References Cited

U.S. PATENT DOCUMENTS

| | | | |
|---|---|---|---|
| 4,673,355 A * | 6/1987 | Farris | C01B 25/32 433/218 |
| 8,790,681 B2 * | 7/2014 | Altschuler | A61L 27/20 424/423 |
| 2006/0257492 A1 * | 11/2006 | Wen | A61K 9/0024 424/489 |
| 2013/0224277 A1 * | 8/2013 | Amedee | A61L 27/12 424/423 |

FOREIGN PATENT DOCUMENTS

WO    2014169236 A1    10/2014

OTHER PUBLICATIONS

Fujishiro et al (J Chem Tech Biotechnol, 1993, 57, 349-353). (Year: 1993).*
Kattimani et al (Bone and Tissue Regeneration Insights, 2016:7, 9-19). (Year: 2016).*
Hulsart-Billström, Gry et al., "Morphological differences in BMP-2-induced ectopic bone between solid and crushed hyaluronan hydrogel templates," Journal of Materials Science: Materials in Medicine, 2013, p. 1201-1209, vol. 24 No. 5, Springer Science+Business Media, USA.
Hulsart-Billström, Gry et al., "Calcium phosphates compounds in conjunction with hydrogel as carrier for BMP-2: A study of ectopic bone formation in rats," Acta Biomaterialia, Aug. 2011, p. 3042-3049, vol. 7 No. 8, Elsevier Ltd., The Netherlands.
Fricain, J. C. et al. "A nano-hydroxyapatite—Pullulan/dextran polysaccharide composite macroporous material for bone tissue engineering" *Biomaterials*, 2013, pp. 2947-2959, vol. 34.

* cited by examiner

*Primary Examiner* — Celeste A Roney
(74) *Attorney, Agent, or Firm* — Saliwanchik, Lloyd & Eisenschenk

(57) ABSTRACT

The composition for bone regeneration, comprises a) a first phase (3) comprising a plurality of cross-linked hydrogel chunks (1) having a mean diameter of less than 1000 µm and incorporating an amount of mineral particles (2); and b) a second phase (4) comprising a physiologically-compatible aqueous liquid acting as a carrier for the chunks; the chunks being embedded in the second phase (4). The mineral particles (2) have a mean diameter of less than 10 µm and the amount of the mineral particles (2) is less than 20 weight-% of the first phase.

18 Claims, 2 Drawing Sheets

COMPOSITION FOR BONE REGENERATION

BACKGROUND OF THE INVENTION

The invention relates to a composition for bone regeneration according to the preamble of claim 1, to a method according to the preamble of claim 24 for producing cross-linked hydrogel chunks and to application methods according to the claims 26, 27 and 28.

Bone defects can occur in the human body due to many reasons such as trauma, tumors or infections. Depending on the location and the size of the bone defect, it can exceed the body's capabilities of self-repair so that surgeons or dentists have to interfere.

The standard treatment for bone defects is a filling with either autologous bone that is taken from another site of the patient or commercially available bone substitutes. Those bone substitutes are typically either made from processed bone allografts or xenografts (usually bovine) or synthetic materials such as calcium phosphates. The surgeons can choose from solid bone matrix blocks, granules, powders or pastes for which the mineral components are mixed with small amounts of water or gel in order to make them malleable or injectable. There are furthermore also calcium phosphate-based bone cements that are initially well injectable at the time of application, but harden in situ under formation of a big compact calcium phosphate block. The high content of barely resorbable mineral component is one of the major disadvantages of the commercially available materials. Even bone substitute pastes, for which the mineral is combined with a liquid or gel component and which are supposed to be easy to apply, are not injectable through reasonable-sized cannula and therefore require a surgical approach for their application.

What is therefore needed is an improved composition for bone regeneration.

It is an object of the invention to provide a composition for bone regeneration which is needle-injectable is situ thereby forming an osteoconductive scaffold for use in minimally invasive atraumatic applications.

The invention solves the posed problem with a composition for bone regeneration comprising the features of claim 1, with a method for producing cross-linked hydrogel chunks comprising the features of claim 24 and application methods for said composition according to claims 26, 27 and 28.

The composition according to the invention comprises a hydrogel matrix and mineral particles and can furthermore contain one or more active agents such as drugs or metal ions. The special characteristic of the material is its biphasic structure: the first phase contains volume-stable, cross-linked hydrogel chunks with incorporated mineral (preferably hydroxyapatite or other calcium phosphate) particles. The mineral content in this cross-linked phase is less than 20% in order to ensure an excellent injectability of the material. It has been shown in rat studies that this low amount of mineral is sufficient to trigger an apposition of body-own mineral and therefore leads to an in-situ formation of mineralized osteoconductive granules that serve as scaffold for new bone formation. Higher amounts (>20%) of mineral particles have resulted in a reduced injectability of the composition and an impaired crosslinking process.

The gel component has the function to retain the particles and keep the volume of the material until the mineralization of the gel has occurred and the biomaterial is replaced by new bone. This first phase can furthermore contain active agents that can either be bound to the particles or just be integrated in the hydrogel.

The second phase comprises or consists of a liquid or hydrogel-like phase embedding the first phase. It preferably comprises drugs or bioactive molecules, preferably for anti-bacterial, bone anabolic or anti-catabolic, osteogenic and/or osteoconductive purposes, either free or combined with calcium-phosphate particles. Its function is to ensure a fast release of the incorporated substances, to render the composition injectable and to assure a three-dimensional architecture useful for promoting new bone formation through the void spaces in between the mineralizing cross-linked hydrogel chunks.

The main advantage of this composition, compared to the state of the art materials, is its excellent injectability which is mainly caused by the low mineral content. This property is also the reason for the special suitability of the composition for a minimal-invasive application to difficult-to-access bone defects and to bone regions for which the application of state of the art materials requires a surgical approach.

Currently known bone substitutes with hydrogel components comprise typically only non-cross-linked polymer chains that improve the injectability of the materials. Non-crosslinked natural hydrogels, however, are degraded in the human body within days and are not volume stable. Therefore only very low concentrations of non-crosslinked hydrogel can be added to the slowly degradable mineral component as otherwise a lasting defect filling cannot be reached. Attempts have been also made to combine a mineral component with already pre-crosslinked hydrogels (for example commercially available dermal fillers). However, the presence of mineral-free hydrogel chunks, in worst case in combination with hyaluronidase inhibitors that slow down the degradation, leads to the creation of dead voids in bone as bone tissue cannot enter the dense cross-linked hydrogel. The composition according to the invention overcomes this limitation by using only particle containing cross-linked hydrogel that mineralizes via apposition of body-own mineral in a rate which is similar to hydrogel degradation rate. The easily injectable cross-linked hydrogel component is this way transformed into an excellent osteoconductive bone scaffold via an in vivo process without volume loss.

Furthermore, the bi-phasic nature of the composition allows the integration of active agents with tailored release profiles. Depending on the location of the active substance (cross-linked first phase vs non-crosslinked second phase, free molecules vs molecules loaded on carrier particles), either an immediate burst release or a prolonged release profile can be targeted.

Further advantageous embodiments of the invention can be commented as follows:

In a special embodiment the mineral particles have a mean diameter of less than 5 μm, preferably of less than 1 μm.

In a further embodiment the mineral particles may be loaded on their surface with one or more of the following substances:

drugs or bioactive molecules, preferably chosen from
   a) the group of anabolic or anti-catabolic bone active substances, in particular: strontium ranelate, growth factors, anti-sclerostin antibodies, bisphosphonates, selective estrogen receptors or RANK ligand inhibitors; or b) the group of anti-bacterial substances in particular antibiotics, halogen-releasing compounds, peroxides, biguanides, chlorhexidine or c) metals, in particular silver, zinc or copper compounds.

The advantage of this embodiment lies in the fact that the drugs are—especially when they are linked to the comparatively large mineral particles—released slowly over a long time due to the fact that they are enclosed in the cross-linked, mineralizing hydrogel chunks.

The mineral particles may be any calcium phosphates, preferably chosen from the group of:

calcium pyrophosphate $[Ca_2P_2O_7]$, calcium carbonate $[CaCO_3]$, monocalcium phosphate monohydrate $[Ca(H_2PO_4)_2 \cdot H_2O]$, monocalcium phosphate $[Ca(H_2PO_4)_2]$, anhydrous dicalcium phosphate $[CaHPO_4]$, dicalcium phosphate dihydrate $[CaHPO_4 \cdot 2H_2O]$, octocalcium phosphate $[Ca_8H_2(PO_4)_6 \cdot 5H_2O]$, alpha-tricalcium phosphate [alpha-$Ca_3(PO_4)_2$], beta-tricalcium phosphate [beta-$Ca_3(PO_4)_2$], hydroxy-apatite $[Ca_5(PO_4)_3OH]$, tetracalcium phosphate $[Ca_4(PO_4)_2O]$, calcium-deficient hydroxyapatite $[Ca_{10-x}(HPO_4)_x(PO_4)_{6-x}(OH)_{2-x}]$, fluoroapatite $[Ca_5(PO_4)_3F]$, amorphous calcium phosphate oxyapatite $[Ca_{10}(PO_4)_6O]$ or Ca- and P-containing bioactive silica glasses.

Preferably the mineral particles are essentially free of pores.

In a further embodiment the cross-linked hydrogel chunks have a mean diameter in the range of 100-250 μm. The maximum volume of the cross-linked hydrogel chunks is preferably in the range of $4*10^{-9}$ mm$^3$ to 4 mm$^3$.

The hydrogel used for obtaining the cross-linked chucks comprises purposefully a polymeric material, preferably chosen from the group of polysaccharides, in particular hyaluronic acid and derivatives thereof, heparin, heparan sulfate, chondroitin sulfate, dermatan sulfate, keratin sulfate, chitin, chitosan, agarose or agar, collagen, gelatin, elastin or fibrin.

The content of the mineral particles is purposefully in the range of 1-10 weight-%, preferably 2-5 weight-% of the first phase.

The mineral particles may have a volume larger than $1.0*10^{-7}$ μm$^3$, preferably larger than $2.0*10^{-6}$ μm$^3$. The mineral particles (2) may have a volume smaller than $50*10^3$ μm$^3$, preferably smaller than $5*10^3$ μm$^3$.

In a special embodiment the mineral particles are in the shape of needles. The needles may have a length in the range of 10-200 nm, preferably in the range of 40-60 nm.

In a further embodiment the volume of the mineral particles is in the range of $2.0*10^{-7}$-$5.0*10^3$ μm$^3$.

In a further embodiment the first phase has a water content of 75 to 99 weight-%.

Still in a further embodiment the second phase additionally comprises nano- to micro-sized calcium phosphate particles. The nano- to micro-sized calcium phosphate particles may be are chosen from the group of:

calcium pyrophosphate $[Ca_2P_2O_7]$, calcium carbonate $[CaCO_3]$, monocalcium phosphate monohydrate $[Ca(H_2PO_4)_2 \cdot H_2O]$, monocalcium phosphate $[Ca(H_2PO_4)_2]$, anhydrous dicalcium phosphate $[CaHPO_4]$, dicalcium phosphate dihydrate $[CaHPO_4 \cdot 2H_2O]$, octocalcium phosphate $[Ca_8H_2(PO_4)_6 \cdot 5H_2O]$, alpha-tricalcium phosphate [alpha-$Ca_3(PO_4)_2$], beta-tricalcium phosphate [beta-$Ca_3(PO_4)_2$], hydroxy-apatite $[Ca_5(PO_4)_3OH]$, tetracalcium phosphate $[Ca_4(PO_4)_2O]$, calcium-deficient hydroxyapatite $[Ca_{10-x}(HPO_4)_x(PO_4)_{6-x}(OH)_{2-x}]$, fluoroapatite $[Ca_5(PO_4)_3F]$, amorphous calcium phosphate or oxyapatite $[Ca_{10}(PO_4)_6O]$.

The amount of nano- to micro-sized calcium phosphate particles in the second phase may be in the range of 1-40 weight-%, preferably 10-20 weight-%.

The nano- to micro-sized calcium phosphate particles may be loaded on their surface with one or more of the following substances:

a) drugs or bioactive molecules, preferably chosen from the group of: anabolic or anti-catabolic bone active substances, in particular strontium ranelate, growth factors, anti-sclerostin antibodies, bisphosphonates, selective estrogen receptors or RANK ligand inhibitors; or b) anti-bacterial substances, in particular antibiotics, halogen-releasing compounds, peroxides, biguanides, chlorhexidine; or c) metals, in particular silver, zinc or copper compounds.

The advantage of this embodiment lies in the fact that the drugs are released relatively quickly in a short time due to the fact that they are located in the well accessible physiologically-compatible aqueous liquid acting as a carrier for the chunks. Those substances can also be integrated independently from the calcium phosphate particles as not all substances can be loaded on the particles.

The ratio of the first phase versus the second phase in terms of volume may be in the range of 3:1 to 19:1, preferably in the range of 4:1 to 10:1

In a special embodiment the composition according to the invention is essentially free of a hyaluronidase inhibitor and in particular essentially free of ascorbic acid 6-hexadecanoate.

In a further embodiment the composition is free of a third phase with cross-linked hydrogel having no mineral particles.

In a further embodiment the composition is essentially free of anesthetics.

A method for producing the cross-linked hydrogel chunks used in the composition according to the invention may comprise the following steps:

a) Selecting a hydrogel comprising a polymeric material, preferably chosen from the group of polysaccharides, in particular hyaluronic acid and derivatives thereof, heparin, heparan sulfate, chondroitin sulfate, dermatan sulfate, keratin sulfate, chitin, chitosan, agarose or agar, collagen, gelatin, elastin or fibrin.

b) Admixing mineral particles to the selected hydrogel in order to evenly distribute them within the hydrogel;

c) Crosslinking the mixture obtained in step b) by the action of a cross-linking agent, and d) Fragmenting the cross-linked mixture of step c) in order to obtain chunks with a maximum volume of 4 mm$^3$ The derivatives of hyaluronic acid may be chosen from the group of HA-amine, HA-hydrazide, HA-disulfide, HA-tyramine, methacrylated or esterified hyaluronic acid.

The composition according to the invention is capable to be used in repairing bone defects and augmenting fragile bone structures, in particular in the orthopedic or traumatological field. The composition may further be used in dentistry for the treatment of periodontitis and peri-implantitis-related bone defects or for bone augmentation in particular sinus lift. The composition is also apt for the treatment of periodontal or peri-implant bone defects.

A method for the minimal-invasive application of the composition according to the invention to superficial periodontal or peri-implant bone defects can comprise the following steps:

a) Extensive scaling and root planning of the affected tooth/implant to remove all infected tissues and the plaque/biofilm on the surface of the tooth/implant
b) Application of the composition used in one of the claims 1 to 23 via subgingival injection from the syringe directly into the bone defect The cleaning done during step a) may be done mechanically, in particular by curette, or by means of light, preferably with laser, ultrasound or with water- or air-jet.

Another method for the minimal-invasive application of the composition according to the invention for minimal invasive sinus lift may comprise the following steps:
a) Gaining access to the site to be treated by creation of a gingival flap;
b) Creation of a small opening to the sinus cavity by means of drilling or punching
c) Elevation of the Schneiderian membrane, preferably with a balloon; and
d) Filling of the created void via an injection of the composition according to the invention through the opening that was created in step b).

A further method for the minimal-invasive application of the composition according to the invention for bone augmentation in orthopedics, in particular for the treatment of the femoral neck or the vertebrae, may comprise the following steps:
a) Gaining access to the targeted bone via a very small soft tissue incision or purposefully sized cannula or trocar.
b) Creation of an opening of less than 1 mm in the cortex of the bone by means of drilling or punching;
c) Application of the composition according to the invention via an injection from a syringe into the trabecular bone; and
d) Closing of the soft tissues.

Detailed Description of the First Phase

The hydrogel of the first phase can be made of any suitable biocompatible and degradable polymeric material that can be cross-linked in order to achieve a dense gel structure. The hydrogel comprises or consists preferably of natural polymeric material (i.e., non-synthetic polymers, polymers that can be found in nature) and/or polymers derived from ECM such as gelatin, elastin, collagen, agar/agarose, chitosan or fibrin. They may also comprise either at least one glycosaminoglycan or at least one proteoglycan, or a mixture thereof. The glycosaminoglycan may be for example a hyaluronic acid, chondroitin sulfate, dermatan sulfate, keratan sulfate or combinations thereof. Natural and ECM derived polymers are first choice biomaterials due to their biological and chemical similarities to natural tissues.

The preferred embodiment according to the invention for the cross-linked first phase hydrogel is hyaluronic acid or derivatives thereof. In experimental settings, an aqueous solution hyaluronic acid with a molecular weight of 2 million Daltons has been used, with a concentration spanning from 1 to 2% w/v, but concentrations spanning from 0.1 to 5% w/v can be envisaged. No particular method for obtaining the cross-linked hyaluronic acid is preferable; any kind of known non-crosslinked hyaluronic acid composition can be used as long as it permits the incorporation of micro/nanoparticles in the cross-linked gel before polymerization.

In experimental settings, BDDE (1,4-butanediol diglycidyl ether) was used as a crosslinking agent with a 0.00273 v/v concentration (27.3 µl in 10 ml of final gel). The final gel was purposefully dialyzed after the crosslinking step in order to remove free unreacted BDDE.

After crosslinking, the cross-linked first phase was extruded through a 160 µm mesh filter in order to obtain evenly sized chunks of that size. Chunk size is chosen based on the size of the needle/cannula used for the injection of the final material and the structure of the targeted bone region; this size can preferably vary from 50 to 500 µm.

The first phase hydrogel acts basically as a bulking element in order to fill the volume of a bone defect such as periodontal/peri-implant defects. It furthermore retains the mineral particles that act as "nucleation points" that induce a mineralization of the phase itself. The forming mineralized granules act as in situ-forming osteoconductive scaffold that guides and supports new bone formation.

The first phase can furthermore contain within it bioactive substances that would be released as long as the first phase mineralization goes on, which will be in any case a slow process compared to what will be described later on for the non-crosslinked second phase drug release.

The first phase hydrogel comprises calcium phosphate particles which have the main function of inducing the mineralization of the first phase. In the preferred embodiment, hydroxyapatite particles are chosen, as they have been shown to efficiently induce mineralization. The size of the particles can range from about 50 nm to about 5 µm. Experimental results showed that better results can be obtained with nanosized particles as they have a higher mineralization activity, and therefore seem to link a small particle size to a better mineralization performance. The particles can be substantially round in shape, but 50 nm needle-shaped particles have also been used, showing excellent results. In one embodiment, also 200 nm round or 5 µm round particles have been used. In two particular embodiments, hydroxyapatite particles <50 nm with a BET surface area ≥80 $m^2/g$ or hydroxyapatite particles of 5±1 µm with a BET surface area ≥100 $m^2/g$ have been used. When using a scanning electron microscope (SEM) for visualization, the particles looks substantially smooth on their surface and present no significant porosity in their core.

The concentration of the calcium phosphate particles is preferably comprised between 1 to 20% w/v of the first phase gel, preferably between 1 and 5%. Higher concentrations are not contemplated because of resulting difficulties in injectability of the final gel and crosslinking. As shown in an experimental set-up, a 1 to 2% concentration is sufficient to efficiently trigger a good mineralization process.

The particles are added to the first phase hydrogel before the crosslinking process, and they are evenly distributed therein in order to induce a homogeneous mineralization process.

In an in vivo setting, the mineralization rate of the first phase comprising a cross-linked hyaluronic acid hydrogel as described incorporating a low concentration of hydroxyapatite micro/nanoparticles (10% w/v of final first phase hydrogel), either loaded or not with bisphosphonates (in one embodiment, Zoledronate) has been studied with microCT-based dynamic histomorphometry. The results of the combined material showed a doubled or tripled mineralization rate 3 to 10 days after application into the femoral condyles of rats when comparing to a crosslinked hyaluronic acid hydrogel without hydroxyapatite. This parameter is based on the comparison of two consecutive microCT scans obtained 3 or 10 days after hydrogel implantation. The mineralization rate is given in %/day and calculated with the ratio of newly created mineralized matrix and previously present mineralized matrix.

Detailed Description of the Second Phase:

The second phase comprises a physiologically-compatible liquid such as water, buffer solutions like PBS or even a non-cross-linked hydrogel material such as non-crosslinked hyaluronic acid. The second phase embeds the first phase and in certain aspects it works as a carrier for it. When a hyaluronic acid hydrogel is used, the concentration thereof would preferably be in the same range as for the first phase hyaluronic acid hydrogel (spanning from 0.1 to 5% w/v), and preferably a low molecular weight hyaluronic acid (less than 1 million Daltons) would be used due to its better anti-inflammatory effect in vivo.

Moreover, the second phase can comprise bioactive substances within it such as preferably antibacterial/antibiotic agents, analgesics, cytokines, growth factors, proteins, peptides, small molecule drugs such as for instance an osteoinductive agent, an osteoconductive agent, an anti-resorptive agent or any combination thereof. Depending on the size of the bioactive substances, they can freely diffuse from the second to the first phase and back, or they can be confined in the second phase: therefore the size of the bioactive compound and/or other physico-chemical parameters of the phases (e.g. concentration) influences the release of the active substances once the material is implanted/injected in a subject's body. For instance, free silver ions used as antibacterial agent will be released faster than larger silver particles. Silver is one of the most preferred bioactive and antibacterial substances to be incorporated in the second phase, particularly for dental applications where an infectious process is often a cause of bone loss. Silver is applied either in form of particles, free ions or ions loaded on the surface of calcium phosphate particles as previously described.

In a preferred embodiment, the second phase comprises calcium phosphate particles as described before, possibly loaded with any of the above-mentioned bioactive substances. In a preferred embodiment, such particles are loaded with bisphosphonates and/or silver ions. This kind of combinations would enhance the bone formation process while avoiding possible infectious processes; this combination is particularly interesting for dental bone defects. The loading process can consist in dissolving the active substance in a suitable solvent such as water and then either adding the micro-particles or mixing the active substance solution obtained with a nanoparticle dispersion. The final product will be a micro/nanoparticle coated on its surface with the bioactive substance.

Being a flowable, fluid phase, the second phase facilitates the injection of the final hydrogel and leaves at the same time space between the cross-linked chunks for neovascularization and new bone formation.

The first phase vs second phase ratio in terms of volume is preferably 4:1, but can go up to 19:1 in order to remain injectable.

Applications

The described composition according to the invention is preferable stored in and applied from a syringe. The soft consistency and unique injectability of the material makes it especially suitable for irregular-shaped, non-load-bearing, confined and difficult to access bone defects. Those kinds of defects can be found in the orthopedic, traumatological, aesthetic and the dental medicine.

In dentistry, due to it's much more favorable injectability (easily passes 25G needles) compared to currently used bone substitutes, the material can be applied to peri-implant and periodontal defects with a flap-less minimal invasive technique. Bone defects surrounding natural teeth or dental implants in patients affected by periodontitis or peri-implantitis can be filled by a simple sub-gingival injection of the material after a proper cleaning and disinfection of the site as shown in FIG. 5.

Another possible application for the new biomaterial is a minimal-invasive sinus lift for which bone substitute is injected in a void in the sinus created by an elevation of the Schneiderian membrane for example with a balloon as shown in FIG. 6. Again, due to the excellent injectability of the new biphasic material, only a very small atraumatic access is necessary for the application of the material. An additional benefit of the new material is that it can be completed with an antibacterial agent such as silver-ions. This makes it perfectly suitable for bone defects created by infectious processes such as peri-implantitis.

Beside the minimal invasive treatment of smaller bone defects, the composition according to the invention can also be used for the surgical treatment of larger defects in combination with a membrane that is used to retain the material in place. This is a standard procedure that is also used for most other commercially available bone substitutes.

The composition according to the invention has also big advantages in traumatology and orthopedics. It is preferably used for confined, difficult-to-access bone defects caused by trauma, cysts, tumors or others. Like for dental applications, only a minimal invasive access to the site is needed in order to apply the material. Another possible application is the prophylactic application of the material into impaired, fragile bone structures such as the femoral neck or in vertebrae of osteoporotic patients via a simple intraosseous injection. The material can also be applied to predrilled bone screw holes or the prepared beds of other implants (e.g. hip, knee, shoulder) for a local augmentation of the bone structure. This application has been tested in combination with a bisphosphonate in an osteoporotic rat model with favorable results. An integrated anti-microbial agent furthermore reduces the risk of dangerous implant infections.

Beside the injectable form of the composition according to the invention, a second lyophilized and spongy form of the material is also possible. The lyophilized hyaluronic acid readily absorbs body fluids leading to an in-situ-formation of the hydrogel. The spongy form can be favorable for an application to larger, open bone defects in the frame of an open surgical intervention.

A BRIEF DESCRIPTION OF THE DRAWINGS

A special embodiment of the invention will be described in the following by way of example and with reference to the accompanying drawings in which.

DETAILED DESCRIPTION OF THE INVENTION

Figure 1:
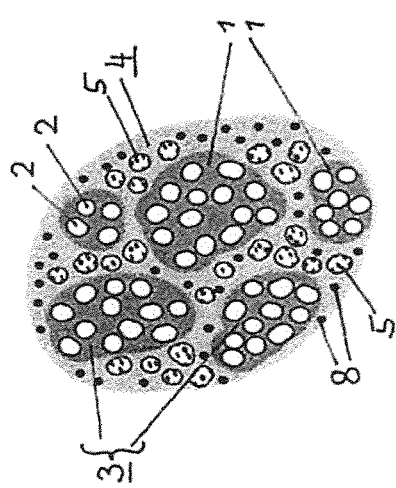
FIG. 1 illustrates schematically a special embodiment of the composition according to the invention immediately after injection into a defective bone area.

The composition according to the invention shown in FIG. 1 consist of a first phase 3 comprising a plurality of cross-linked hydrogel chunks 1 with mineral particles 2 incorporated therein. These cross-linked hydrogel chunks 1 are embedded in a second phase 4 comprising a physiologically-compatible aqueous liquid acting as a carrier for the chunks 1. Preferably the second phase is a physiological liquid or non-cross-linked hydrogel with mineral particles 5 which can be loaded at their surface with a drug 6.

The second phase 4 may also comprise free drugs 8. Free drug molecules 8 will be released the fastest, particle-bound drug substances in mineral particles 5 in the second phase will be released a bit slower and the substances bound to the mineral particles 2 in the first phase will have the slowest release.

Figure 2:
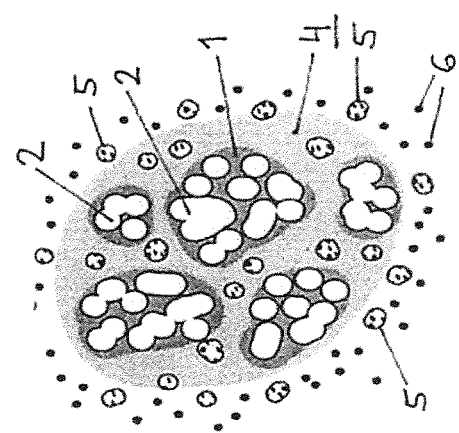
FIG. 2 illustrates schematically the composition of FIG. 1 after a first period of time has elapsed upon injection into a defective bone area.

In FIG. 2 it is shown how after some time has elapsed after injection of the composition into a bone defect. The mineral particles 5 and the free drugs 8, if in the second phase 4, are released from that second phase 4. Since the second phase 4 is not cross-linked the release of its mineral particles 5 and especially the free drugs 8 occurs rather quickly and consequently the drug 6 loaded on the surface of the mineral particles 5 is also released rather quickly.

At same time there is a continuous mineral deposition from the body into the cross-linked chucks 1 while the hydrogel of the chunks is degrading.

Figure 3:
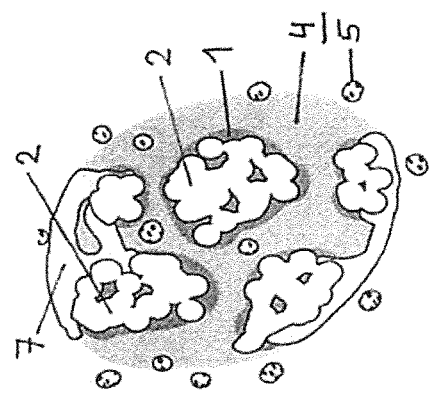
FIG. 3 illustrates schematically the composition of FIG. 2 after some further time.

In FIG. 3 it is shown how, after some further time, mineral granules 2 are forming from the chunks 1 and bone ingrowth is guided by these osteoconductive mineral granules 2.

Figure 4:
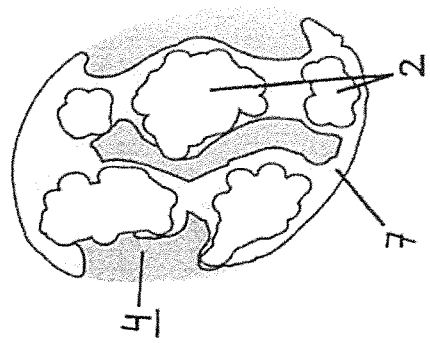
FIG. 4 illustrates schematically the composition of FIG. 3 after some further time

In FIG. 4 it is shown how, after some further time, the mineral granules 2 formed from the chunks 1 are incorporated into newly formed bone 7.

Figure 5:
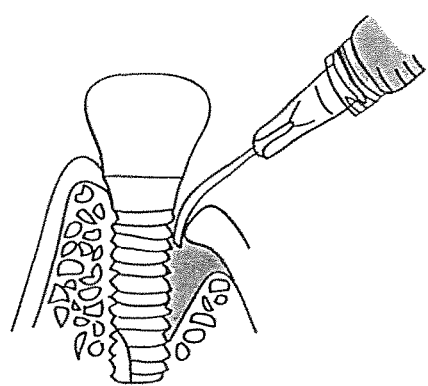
FIG. 5 illustrates an application of the composition according to the invention for the minimal-invasive peri-implantitis treatment.

In FIG. 5 an application of the composition according to the invention for minimal-invasive peri-implantitis treatment is illustrated via subgingival injection from a syringe directly into the bone defect.

Figure 6:
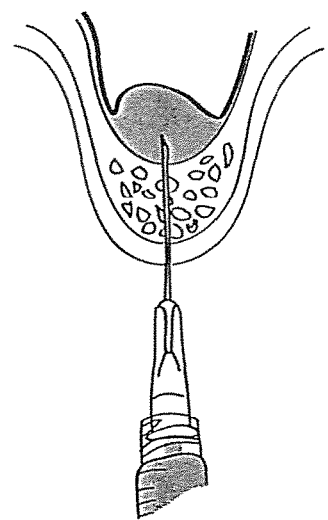
FIG. 6 illustrates an application of the composition according to the invention for the minimal invasive sinus lift treatment.

In FIG. 6 an application of the composition according to the invention for minimal invasive sinus lift treatment is illustrated by creation of a gingival flap and of a small opening to the sinus cavity by means of drilling or punching, subsequent elevation of the Schneiderian membrane and filling of the created void via a sub-gingival injection of the composition according to the invention through the opening that was created from a syringe directly into the bone defect.

The following examples clarify the invention further in more detail.

Example 1

Preparation of the first phase: 400 mg of hydroxyapatite particles (rounded shape, average diameter of 5 μm) were mixed with 0.1 ml NaOH 5M and 1.873 ml of $H_2O$. 200 mg of hyaluronic acid sodium salt (molecular weight 2 MDa) were added to the particle suspension. The resulting mixture was homogenized with a stirrer. 27.3 μl of the crosslinker BDDE (1,4-butanediol diglycidyl ether) were added and homogenized for 1 hour. The mixture was then kept at 60° C. during 3 hours for crosslinking. Afterwards, the reaction was stopped by placing the material in the fridge at 4° C. and the mixture was neutralized by an addition of 0.5 ml HCl 1M and 7.5 ml $H_2O$. After complete swelling of the hydrogel, it was dialyzed for 48 hours in PBS in order to remove unreacted crosslinker and crushed down to an average particle size of 100 μm by extrusion through a filter. The final water content of the first phase was around 97%.

Preparation of the second phase: Hydroxyapatite particles were loaded with the bisphosphonate Zoledronate. Therefore, an aqueous Zoledronate stock solution with a concentration of 3 mg/ml was prepared. 200 mg of hydroxyapatite particles (rounded shape, average diameter of 5 μm) were mixed with 0.8 ml $H_2O$ and a 4 μl Zoledronate stock solution.

In a third step, the first and second phase of the composition were mixed with a ratio of 10:1, filled in a syringe and heat sterilized.

The resulting composition could be easily injected through a 25G needle and achieved favorable results in vivo in a rat defect model.

Example 2

Preparation of the first phase: 1 g of tricalcium phosphate particles (rounded shape, average diameter of 3 μm) were mixed with 0.1 ml NaOH 5M and 1.873 ml of $H_2O$. 200 mg of hyaluronic acid sodium salt (molecular weight 2 MDa) were added to the particle suspension. The resulting mixture was homogenized with a stirrer. 27.3 μl of the crosslinker BDDE (1,4-butanediol diglycidyl ether) were added and homogenized for 1 hour. The mixture was then kept at 60° C. during 3 hours for crosslinking. Afterwards, the reaction was stopped by placing the material in the fridge at 4° C. and the mixture was neutralized by an addition of 0.5 ml HCl 1M and 7.5 ml $H_2O$. After complete swelling of the hydrogel, it was dialyzed for 48 hours in PBS in order to remove unreacted crosslinker and crushed down to an average particle size of 150 μm by extrusion through a filter. The final water content of the first phase was around 94%.

Preparation of the second phase: Tricalcium phosphate particles were loaded with the bisphosphonate Zoledronate. Therefore, an aqueous Zoledronate stock solution with a concentration of 3 mg/ml was prepared. 200 mg of tricalcium phosphate particles (rounded shape, average diameter of 3 μm) were mixed with 0.8 ml $H_2O$ and a 4 μl Zoledronate stock solution. 8 mg of non-crosslinked hyaluronic acid sodium salt (molecular weight 50 kDa) were added to the dispersion.

In a third step, the first and second phase of the composition were mixed with a ratio of 4:1, filled in a syringe and heat sterilized.

The resulting composition could be easily injected through a 25G needle.

Example 3

Preparation of the First Phase: According to Example 1

Preparation of the second phase: Hydroxyapatite particles (rounded shape, average diameter of 200 nm) were impregnated with silver ions by an immersion of the particles in a $8*10^{-5}$ mol/l silver nitrate solution. 200 mg of the loaded particles were then mixed with 0.8 ml $H_2O$. 8 mg of non-crosslinked hyaluronic acid sodium salt (molecular weight 50 kDa) were added to the dispersion.

In a third step, the first and second phase of the composition were mixed with a ratio of 6:1, filled in a syringe and heat sterilized.

The resulting composition could be easily injected through a 25G needle.

Example 4

Preparation of the first phase: 2 g of octacalcium phosphate particles (irregular shape, average diameter of 1 μm) were mixed with 0.1 ml NaOH 5M and 1.873 ml of $H_2O$. 200 mg of hyaluronic acid sodium salt (molecular weight 2 MDa) were added to the particle suspension. The resulting mixture was homogenized with a stirrer. 27.3 μl of the crosslinker BDDE (1,4-butanediol diglycidyl ether) were added and homogenized for 1 hour. The mixture was then kept at 60° C. during 3 hours for crosslinking. Afterwards, the reaction was stopped by placing the material in the fridge at 4° C. and the mixture was neutralized by an addition of 0.5 ml HCl 1M and 7.5 ml H2O. After complete swelling of the hydrogel, it was dialyzed for 48 hours in PBS in order to remove unreacted crosslinker and crushed down to an average particle size of 160 μm by extrusion through a filter. The final water content of the first phase was around 89%.

Preparation of the second phase: Octacalcium phosphate particles were loaded with the bisphosphonate Ibandronate. Therefore, an aqueous Ibandronate stock solution with a concentration of 30 mg/ml was prepared. 300 mg of Octacalcium phosphate particles (irregular shape, average diameter of 1 μm) were mixed with 0.8 ml $H_2O$ and a 4 μl Ibandronate stock solution. 50 mg of silver nanoparticles (irregular shape, average diameter of 5 nm) were added to the dispersion.

In a third step, the first and second phase of the composition were mixed with a ratio of 5:1, filled in a syringe and heat sterilized.

The resulting composition could be easily injected through a 25G needle.

The composition according to the invention is useful for bone defect repair or bone augmentation particularly in dentistry, orthopedics and traumatology. Thanks to the excellent injectability of the composition, a simple intraosseous injection of the material in fragile bone regions is possible. The material may also be injected sub-gingivally for treating periodontitis- or peri-implantitis-related bone defects (see FIG. 5), or into the sinus for a minimal-invasive sinus augmentation (see FIG. 6).

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A composition comprising:
a) a gel phase as a first phase comprising a plurality of cross-linked hydrogel chunks having a mean diameter of less than 1000 μm and wherein an amount of mineral particles are incorporated in said cross-linked hydrogel chunks; and
b) an aqueous phase as a second phase comprising a physiologically-compatible aqueous liquid that acts as a carrier for the chunks, the chunks being embedded in the second phase;
wherein:
the mineral particles have a mean diameter of less than 10 μm; and
the amount of the mineral particles is less than 20 weight-% of the first phase; and
wherein the composition is formulated as an injectable composition for bone regeneration.

2. The composition according to claim 1, wherein the mineral particles have a mean diameter of less than 5 μm.

3. The composition according to claim 1, wherein the second phase further comprises nano- to micro-sized calcium phosphate particles selected from the group consisting of calcium pyrophosphate, calcium carbonate, monocalcium phosphate monohydrate, monocalcium phosphate, anhydrous dicalcium phosphate, dicalcium phosphate dihydrate, octocalcium phosphate, alpha-tricalcium phosphate, beta-tricalcium phosphate, hydroxyapatite, tetracalcium phosphate, calcium-deficient hydroxyapatite, fluoroapatite, amorphous calcium phosphate and oxyapatite,
wherein one or more substances are loaded on a surface of the mineral particles, said one or more substances being selected from the group consisting of:
a)
drugs,
bioactive molecules,
anabolic bone active substances,
anti-catabolic bone active substances,
strontium ranelate,
growth factors,
anti-sclerostin antibodies,
bisphosphonates,
selective estrogen receptors,
RANK ligand inhibitors; or
b)
anti-bacterial substances,
antibiotics,
halogen-releasing compounds,
peroxides,
biguanides,
chlorhexidine; or
c)
metals,
silver,
zinc, and
copper compounds.

4. The composition according to claim 1, wherein the mineral particles are:
calcium phosphates selected from the group consisting of
calcium pyrophosphate,
calcium carbonate,
monocalcium phosphate monohydrate,
monocalcium phosphate,
anhydrous dicalcium phosphate,
dicalcium phosphate dihydrate,
octocalcium phosphate,
alpha-tricalcium phosphate,
beta-tricalcium phosphate,
hydroxy-apatite,
tetracalcium phosphate,
calcium-deficient hydroxyapatite,
fluoroapatite,
amorphous calcium phosphate oxyapatite;
Ca-containing bioactive silica glasses and P-containing bioactive silica glasses.

5. The composition according to claim 1, wherein the cross-linked hydrogel chunks have a mean diameter from 50 to 500 μm.

6. The composition according to claim 1, wherein the hydrogel of the cross-linked hydrogel chucks is a polymeric material selected from the group consisting of polysaccharides, hyaluronic acid and derivatives thereof, heparin, heparan sulfate, chondroitin sulfate, dermatan sulfate, keratin sulfate, chitin, chitosan, agarose, agar, collagen, gelatin, elastin and fibrin.

7. The composition according to claim 1, wherein the mineral particles are in a shape of needles.

8. The composition according to claim 1, wherein a ratio of the first phase to the second phase in terms of volume is in a range of 3:1 to 19:1.

9. The composition according to claim 1, wherein the composition is essentially free of a hyaluronidase inhibitor.

10. The composition according to claim 3, wherein the mineral particles are loaded with a bisphosphonate.

11. The composition according to claim 1, wherein the mineral particles have a mean diameter of from 50 nm to 5 µm.

12. A method for repairing bone defects and augmenting fragile bone structures comprising injecting the composition according to claim 1 into a bone defect or a fragile bone structure.

13. A method for treating periodontitis and peri-implantitis-related bone defects or for bone augmentation comprising injecting the composition according to claim 1 into a bone.

14. A method for treating periodontal or peri-implant bone defects comprising applying the composition according to claim 1 to a bone.

15. A method for minimally-invasive application of the composition according to claim 1 to superficial periodontal or peri-implant bone defects, the method comprising steps:

a) cleaning by extensive scaling and root planning of an affected tooth/implant to remove all infected tissues and any plaque/biofilm on a surface of the tooth/implant; and b) applying the composition via subgingival injection from a syringe directly into the bone defect.

16. The method according to claim 15, wherein the cleaning done during step a) is done mechanically, by means of light, ultrasound, with a water-jet or with an air-jet.

17. A method for minimally-invasive application of the composition according to claim 1 for a sinus lift, comprising the steps:

a) gaining access to a site to be treated by creating a gingival flap;

b) creating a small opening to a sinus cavity by means of drilling or punching;

c) elevating a Schneiderian membrane; and d) filling a void in an upper jaw area via an injection of the composition through the small opening created in step b).

18. A method for minimally-invasive application of the composition according to claim 1 for bone augmentation in orthopedics, comprising the steps:

a) gaining access to a targeted bone via a very small soft tissue incision or purposefully sized cannula or trocar;

b) creating an opening of less than 1 mm in a cortex of the targeted bone by means of drilling or punching;

c) applying the composition via an injection from a syringe into trabecular bone; and d) closing the soft tissues.

* * * * *